US010530111B2

(12) United States Patent
Srivastava et al.

(10) Patent No.: US 10,530,111 B2
(45) Date of Patent: Jan. 7, 2020

(54) APPARATUS FOR DELIVERING GAS AND ILLUMINATION SOURCE FOR GENERATING HIGH HARMONIC RADIATION

(71) Applicant: ASML Netherlands B.V., Veldhoven (NL)

(72) Inventors: Sudhir Srivastava, Eindhoven (NL); Sander Bas Roobol, Veldhoven (NL); Simon Gijsbert Josephus Mathijssen, Rosmalen (NL); Nan Lin, Eindhoven (NL); Sjoerd Nicolaas Lambertus Donders, Vught (NL); Krijn Frederik Bustraan, Eindhoven (NL); Petrus Wilhelmus Smorenburg, Veldhoven (NL); Gerrit Jacobus Hendrik Brussaard, Boxtel (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/903,392

(22) Filed: Feb. 23, 2018

(65) Prior Publication Data
US 2018/0267411 A1 Sep. 20, 2018

(30) Foreign Application Priority Data

Mar. 15, 2017 (EP) .................................... 17160996
Jun. 13, 2017 (EP) .................................... 17175640
Sep. 4, 2017 (EP) .................................... 17189172

(51) Int. Cl.
*G03F 7/20* (2006.01)
*H01S 3/00* (2006.01)
(Continued)

(52) U.S. Cl.
CPC ....... *H01S 3/0092* (2013.01); *G01N 21/8806* (2013.01); *G03F 7/70883* (2013.01);
(Continued)

(58) Field of Classification Search
None
See application file for complete search history.

(56) References Cited

U.S. PATENT DOCUMENTS

| 5,255,282 A | 10/1993 | Remo |
| 2002/0172235 A1 | 11/2002 | Chang et al. |

(Continued)

FOREIGN PATENT DOCUMENTS

| JP | H07-193301 A | 7/1995 |
| WO | WO 2011/139303 A2 | 11/2011 |

(Continued)

OTHER PUBLICATIONS

Wolterink T.A.W., "High-gradient gas-jet targets for laser wakefield acceleration," University of Twente, Master of Science Thesis, Faculty of Science and Technology, Laser Physics and Nonlinear Optics, Apr. 2011; 80 pages.

(Continued)

*Primary Examiner* — Michelle M Iacoletti
(74) *Attorney, Agent, or Firm* — Sterne, Kessler, Goldstein & Fox P.L.L.C.

(57) ABSTRACT

Disclosed is gas delivery system which is suitable for a high harmonic generation (HHG) radiation source which may be used to generate measurement radiation for an inspection apparatus. In such a radiation source, a gas delivery element delivers gas in a first direction. The gas delivery element has an optical input and an optical input, defining an optical path running in a second direction. The first direction is arranged relative to the second direction at an angle that is not perpendicular or parallel. Also disclosed is a gas delivery (Continued)

element having a gas jet shaping device, or a pair of gas delivery elements, one of which delivers a second gas, such that the gas jet shaping device or second gas is operable to modify a flow profile of the gas such that the number density of the gas falls sharply.

17 Claims, 10 Drawing Sheets

(51) Int. Cl.
*H05G 2/00* (2006.01)
*G03F 1/84* (2012.01)
*G01N 21/956* (2006.01)
*G02F 1/35* (2006.01)
*G01N 21/88* (2006.01)

(52) U.S. Cl.
CPC ............... *H01S 3/00* (2013.01); *H05G 2/008* (2013.01); *G01N 21/956* (2013.01); *G02F 2001/354* (2013.01); *G03F 1/84* (2013.01); *G03F 7/7065* (2013.01); *G03F 7/7085* (2013.01); *G03F 7/70616* (2013.01)

(56) References Cited

U.S. PATENT DOCUMENTS

| | | |
|---|---|---|
| 2006/0006345 A1 | 1/2006 | Smith et al. |
| 2006/0066855 A1 | 3/2006 | Boef et al. |
| 2011/0102753 A1 | 5/2011 | Van De Kerkhof et al. |
| 2012/0044470 A1 | 2/2012 | Smilde et al. |
| 2014/0112362 A1 | 4/2014 | Tanino et al. |
| 2017/0031246 A1 | 2/2017 | Den Boef |
| 2017/0184511 A1 | 6/2017 | Den Boef et al. |
| 2017/0315456 A1 | 11/2017 | Lin et al. |
| 2017/0322497 A1 | 11/2017 | Lin et al. |
| 2018/0136568 A1 | 5/2018 | Roobol et al. |

FOREIGN PATENT DOCUMENTS

| | | |
|---|---|---|
| WO | WO 2017/108410 A1 | 6/2017 |
| WO | WO 2017/186491 A1 | 11/2017 |
| WO | WO 2017/191084 A1 | 11/2017 |
| WO | WO 2018/086816 A2 | 5/2018 |

OTHER PUBLICATIONS

Schmid et al., "Density-transition based electron injector for laser driven wakefield accelerators," The American Physical Society, Physical Review Special Topics—Accelerators and Beams, vol. 13, No. 091301, 2010; pp. 1-5.

Harada Tetsuo et al., "Development of standalone coherent EUV scatterometry microscope with high-harmonic generation EUV source," Visual Communications and Image Processing. vol. 8441, 2012; 10 pages.

Written Opinion and International Search Report of the International Search Authority directed to related International Patent Application No. PCT/EP2018/053772, dated Jun. 6, 2018; 12 pages.

International Preliminary Report on Patentability directed to related International Patent Application No. PCT/EP2018/053772, dated Sep. 17, 2019; 9 pages.

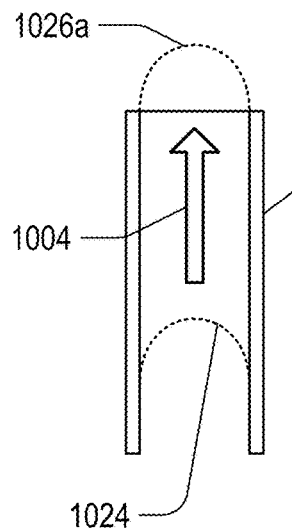
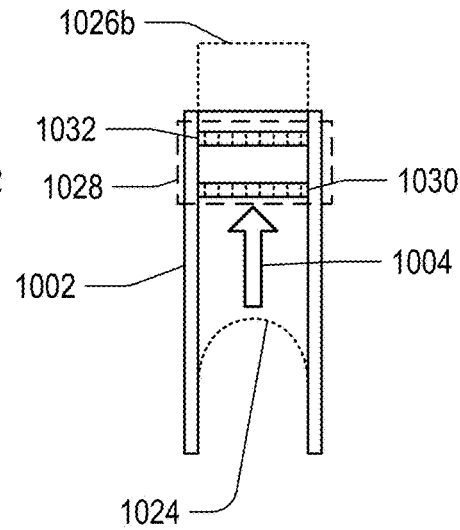
Fig. 10(a)
Fig. 10(b)
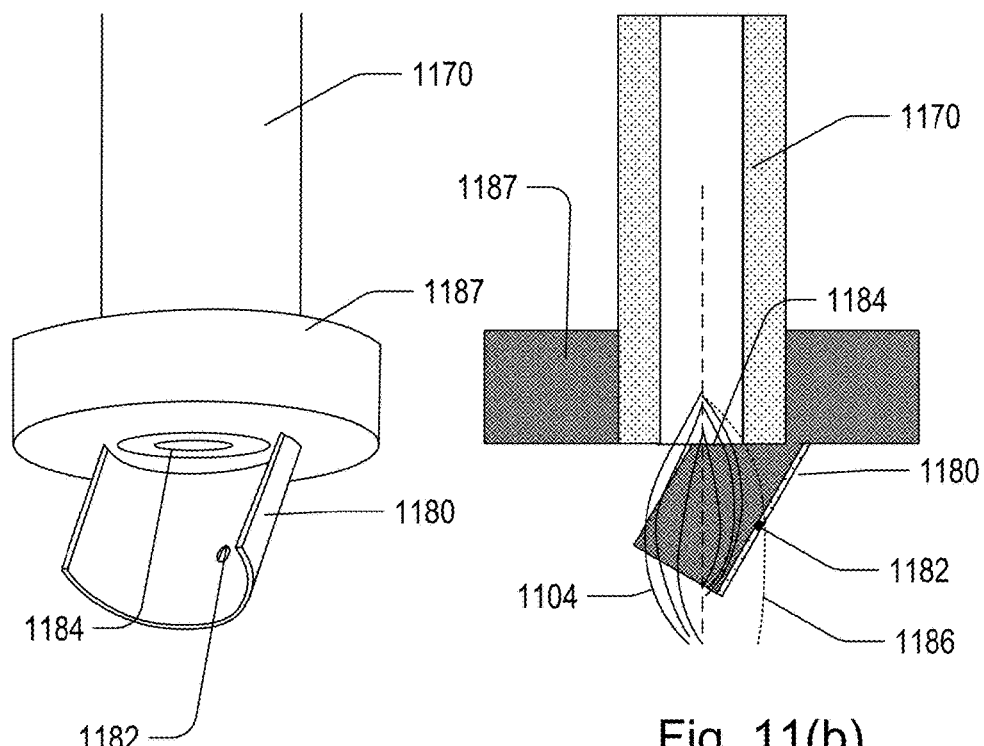
Fig. 11(a)
Fig. 11(b)

APPARATUS FOR DELIVERING GAS AND ILLUMINATION SOURCE FOR GENERATING HIGH HARMONIC RADIATION

CROSS REFERENCE TO RELATED APPLICATIONS

This application incorporates by reference in their entireties EP Patent Application No. 17160996, filed Mar. 15, 2017, EP Patent Application No. 17175640, filed Jun. 13, 2017 and EP Patent Application No. 17189172, filed Sep. 4, 2017.

FIELD

The present invention relates to a gas delivery apparatus, and in particular to a gas delivery apparatus for use in an illumination or radiation system.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Multiple layers, each having a particular pattern and material composition, are applied to define functional devices and interconnections of the finished product.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field.

Examples of known scatterometers often rely on provision of dedicated metrology targets. For example, a method may require a target in the form of a simple grating that is large enough that a measurement beam generates a spot that is smaller than the grating (i.e., the grating is underfilled). In so-called reconstruction methods, properties of the grating can be calculated by simulating interaction of scattered radiation with a mathematical model of the target structure. Parameters of the model are adjusted until the simulated interaction produces a diffraction pattern similar to that observed from the real target.

In addition to measurement of feature shapes by reconstruction, diffraction-based overlay can be measured using such apparatus, as described in published patent application US2006066855A1. Diffraction-based overlay metrology using dark-field imaging of the diffraction orders enables overlay measurements on smaller targets. These targets can be smaller than the illumination spot and may be surrounded by product structures on a wafer. Examples of dark field imaging metrology can be found in numerous published patent applications, such as for example US2011102753A1 and US20120044470A. Multiple gratings can be measured in one image, using a composite grating target. The known scatterometers tend to use light in the visible or near-IR wave range, which requires the pitch of the grating to be much coarser than the actual product structures whose properties are actually of interest. Such product features may be defined using deep ultraviolet (DUV) or extreme ultraviolet (EUV) radiation having far shorter wavelengths. Unfortunately, such wavelengths are not normally available or usable for metrology.

On the other hand, the dimensions of modern product structures are so small that they cannot be imaged by optical metrology techniques. Small features include for example those formed by multiple patterning processes, and/or pitch-multiplication. Hence, targets used for high-volume metrology often use features that are much larger than the products whose overlay errors or critical dimensions are the property of interest. The measurement results are only indirectly related to the dimensions of the real product structures, and may be inaccurate because the metrology target does not suffer the same distortions under optical projection in the lithographic apparatus, and/or different processing in other steps of the manufacturing process. While scanning electron microscopy (SEM) is able to resolve these modern product structures directly, SEM is much more time consuming than optical measurements. Moreover, electrons are not able to penetrate through thick process layers, which makes them less suitable for metrology applications. Other techniques, such as measuring electrical properties using contact pads is also known, but it provides only indirect evidence of the true product structure.

By decreasing the wavelength of the radiation used during metrology (i.e. moving towards the "soft X-ray" wavelength spectrum), it is possible to resolve smaller structures, to increase sensitivity to structural variations of the structures and/or penetrate further into the product structures. One such method of generating suitably high frequency radiation (e.g., soft X-ray and/or EUV radiation) is by using a high harmonic generation (HHG) radiation source. Such a HHG radiation source uses laser radiation (e.g., infra-red radiation) to excite a HHG generating medium, thereby generating high harmonics comprising high frequency radiation.

One problem with generated high frequency radiation is that it is absorbed by any particles present in its path. This requires that the HHG radiation source be kept at near vacuum. Since the HHG generating medium is typically a gas, the generating medium must be carefully controlled to prevent it from absorbing the generated radiation.

A further problem with HHG radiation sources is to maintain a stable output of generated radiation. Any fluctuations in the supply of the HHG generating medium may negatively impact the temporal stability of the radiation output.

SUMMARY

In accordance with a first aspect of the invention, there is provided a gas delivery system for use in an illumination source, comprising a gas delivery element arranged to direct gas in at least a first direction, wherein the gas delivery element comprises:
an optical input; and
an optical output,
wherein the input and the output define an optical path, the optical path being oriented in a second direction, and
wherein the second direction is non-perpendicular and non-parallel to the first direction.

In accordance with a second aspect of the invention, there is provided a gas delivery system for use in an illumination source, comprising: a gas delivery element arranged to direct gas in at least a first direction, wherein the gas delivery element comprises: an optical input and an optical output together defining an optical path, the optical path being oriented in a second direction; and a gas jet shaping device operable to modify a flow profile of the gas such that number density of the gas falls sharply in the direction of the optical output after a pump radiation interaction region where pump radiation interacts with said gas.

In accordance with a third aspect of the invention, there is provided an illumination source for generating high harmonic radiation, comprising:

a pump radiation source operable to emit pump radiation; and a gas delivery system as set out above, operable to receive the emitted pump radiation and to generate said high harmonic radiation.

In accordance with a fourth aspect of the invention, there is provided an inspection apparatus for measuring a target structure on a substrate, comprising:

an illumination source as set out above for generating high harmonic radiation; and a sensing element for receiving high harmonic radiation scattered by the target structure.

In accordance with a fifth aspect of the invention, there is provided a lithographic apparatus comprising an illumination optical system arranged to illuminate a pattern, and a projection optical system arranged to project an image of the pattern onto a substrate, wherein the lithographic apparatus comprises an illumination source as set out above.

In accordance with a fifth aspect of the invention, there is provided a lithographic system comprising:

a lithographic apparatus comprising an illumination optical system arranged to illuminate a pattern, and a projection optical system arranged to project an image of the pattern onto a substrate; and an inspection apparatus as set out above, wherein the lithographic apparatus is arranged to use one or more parameters calculated by the inspection apparatus in applying the pattern to further substrates.

In accordance with a sixth aspect of the invention there is provided a delivery system for use in an illumination source, comprising at least a first gas delivery element operable to emit a first gas and a second gas delivery element operable to emit a second gas in such a way that a number density profile of the first gas is altered by the second gas.

In accordance with a seventh aspect of the invention there is provided an illumination source for generating high harmonic radiation, comprising: a pump radiation source operable to emit pump radiation at a high harmonic generation gas medium thereby exciting said high harmonic generation gas medium within a pump radiation interaction region so as to generate said high harmonic radiation; and an ionization radiation source operable to emit ionization radiation at the high harmonic generation gas medium to ionize said gas at an ionization region between the pump radiation interaction region and an optical output of the illumination source.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 10(a) and 10(b) show a filter component according to an embodiment of the present invention;

FIGS. 11(a) and 11(b) show a gas delivery element according to an embodiment of the present invention comprising a gas jet shaping device;

DETAILED DESCRIPTION OF EXEMPLARY EMBODIMENTS

Before describing embodiments of the invention in detail, it is instructive to present an example environment in which embodiments of the present invention may be implemented.

Figure 1:
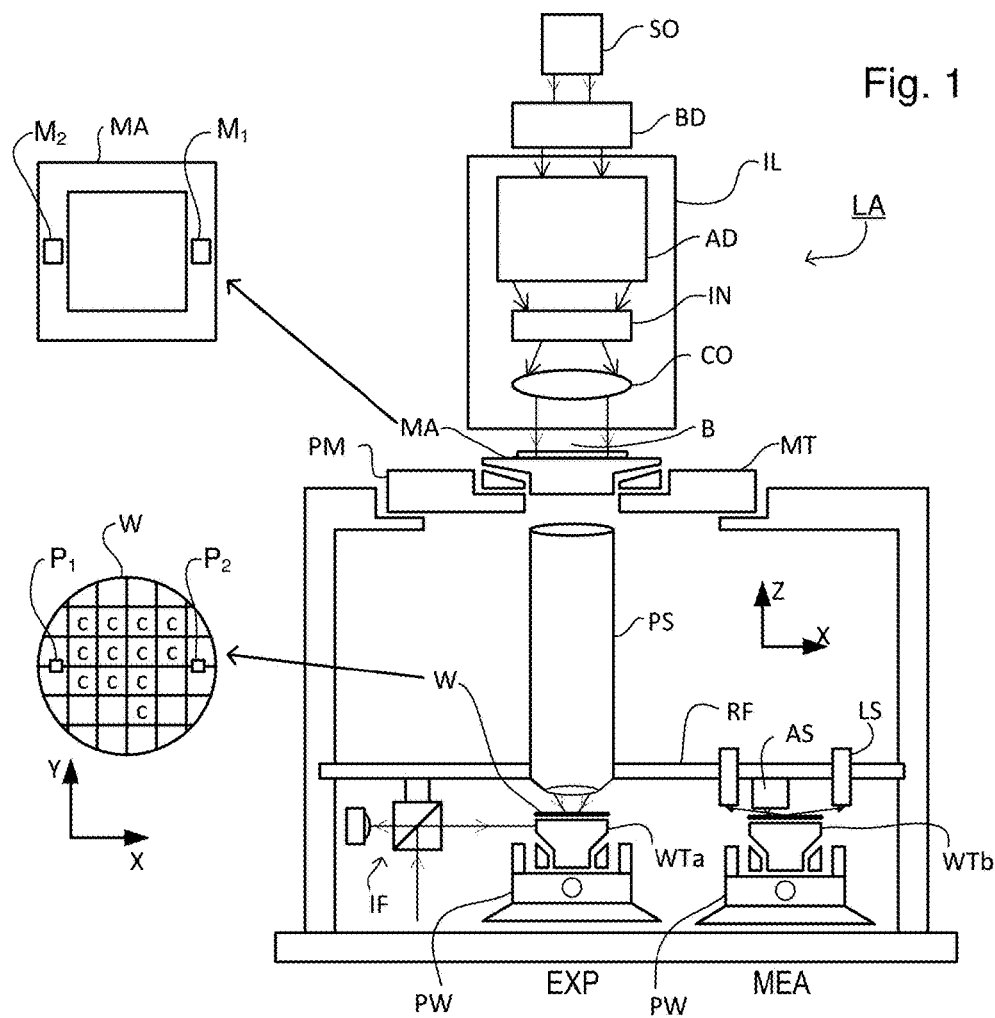
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers, is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
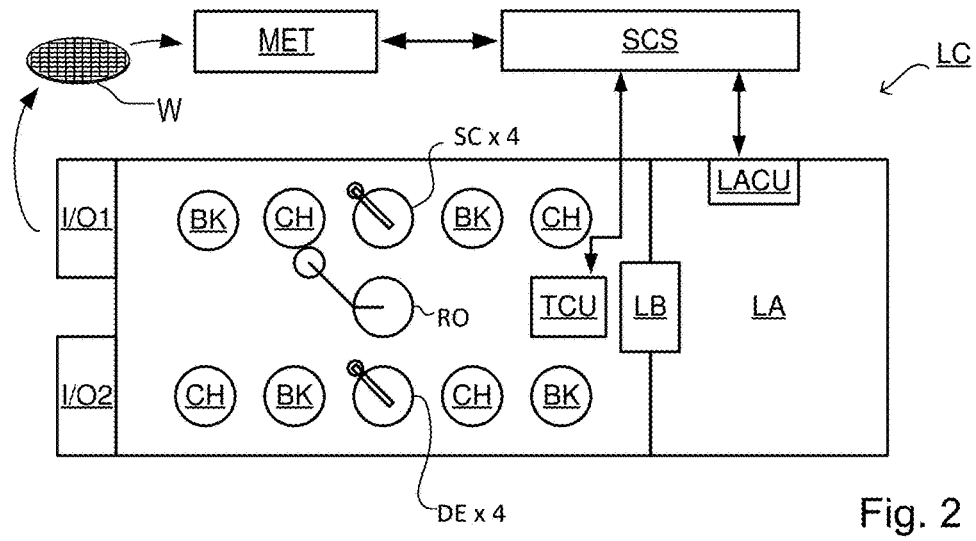
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. The supervisory control system may also control one or more inspection apparatuses MET, used to perform measurements on substrates W to ensure quality and consistency of the lithographic process, and to determine any necessary corrections. Thus, the different apparatus can be operated to maximize throughput and processing efficiency. The substrates processed by the track are then transferred to other processing tools for etching and other chemical or physical treatments within the device manufacturing process.

The lithographic apparatus control unit LACU controls all the movements and measurements of the various actuators and sensors described. LACU also includes signal processing and data processing capacity to implement desired calculations relevant to the operation of the apparatus. In the terminology of the introduction and claims, the combination of these processing and control functions referred to simply as the "controller". In practice, control unit LACU will be realized as a system of many sub-units, each handling the real-time data acquisition, processing and control of a subsystem or component within the apparatus. For example, one processing subsystem may be dedicated to servo control of the substrate positioner PW. Separate units may even handle coarse and fine actuators, or different axes. Another unit might be dedicated to the readout of the position sensor IF. Overall control of the apparatus may be controlled by a central processing unit, communicating with these subsystems processing units, with operators and with other apparatuses involved in the lithographic manufacturing process.

Figure 3A:
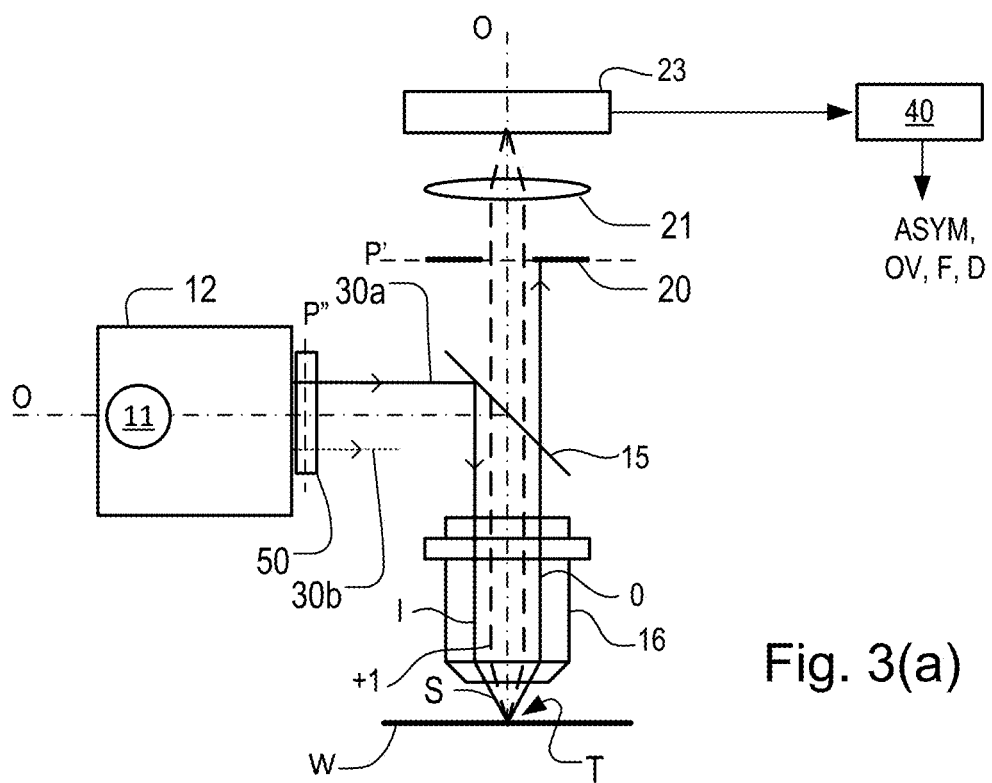
FIGS. 3(a) and 3(b) illustrate schematically an inspection apparatus adapted to perform known dark-field imaging inspection methods.

FIG. 3(a) shows schematically the key elements of an inspection apparatus MET implementing so-called dark field imaging metrology. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating structure T and diffracted rays are illustrated in more detail in FIG. 3(b).

As described in the prior applications cited in the introduction, the dark-field-imaging apparatus of FIG. 3(a) may be part of a multi-purpose angle-resolved scatterometer that may be used instead of or in addition to a spectroscopic scatterometer. In this type of inspection apparatus, radiation emitted by a radiation source 11 (in this disclosure a HHG radiation source) is conditioned by an illumination system 12. For example, illumination system 12 may include a collimating lens system, a color filter, a polarizer and an aperture device. The conditioned radiation follows an illumination path, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired. The multi-purpose scatterometer may have two or more measurement branches. Additionally, further optical systems and branches will be included in a practical apparatus, for example to collect reference radiation for intensity normalization, for coarse imaging of capture targets, for focusing and so forth. Details of these can be found in the prior publications mentioned above. For the purposes of the present disclosure, only the measurement branch of interest for the dark-filed imaging metrology is illustrated and described in detail.

In the collection path for dark-field imaging, imaging optical system 21 forms an image of the target on the substrate W on sensor 23 (e.g. a CCD or CMOS sensor). An aperture stop 20 is provided in a plane P' in the collection path. Plane P' is a plane conjugate to a pupil plane P''' of objective lens 16. Aperture stop 20 may also be called a pupil stop. Aperture stop 20 can take different forms, just as the illumination aperture can take different forms. The aperture stop 20, in combination with the effective aperture of lens 16, determines what portion of the scattered radiation is used to produce the image on sensor 23. Typically, aperture stop 20 functions to block the zeroth order diffracted beam so that the image of the target formed on sensor 23 is formed only from the first order beam(s). In an example where both first order beams are combined to form an image, this would be the so-called dark field image, equivalent to dark-field microscopy. In the present application, however, only one of the first orders is imaged at a time, as explained below. The images captured by sensor 23 are output to image processor and controller 40, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus.

The various components of illumination system 12 can be adjustable to implement different metrology 'recipes' within the same apparatus. In addition to selecting wavelength (color) and polarization as characteristics of the particular, illumination system 12 can be adjusted to implement different illumination profiles. Because plane P''' is conjugate with pupil plane P' of objective lens 16 and the plane of the detector 23, an illumination profile in plane P''' defines the angular distribution of light incident on substrate W in spot S. To implement different illumination profiles, an aperture device can be provided in the illumination path. The aperture device may comprise different apertures mounted on a movable slide or wheel. It may alternatively comprise a programmable spatial light modulator. As a further alternative, optical fibers may be disposed at different locations in the plane P''' and used selectively to deliver light or not deliver light at their respective locations. These variants are all discussed and exemplified in the documents cited above.

In a first example illumination mode, rays 30a are provided so that the angle of incidence is as shown at 'I' and the path of the zero order ray reflected by target T is labeled '0' (not to be confused with optical axis 'O'). In a second illumination mode, rays 30b can be provided, in which case the angles of incidence and reflection will be swapped. Both of these illumination modes will be recognized as off-axis illumination modes. Many different illumination modes can be implemented for different purposes.

Figure 3B:
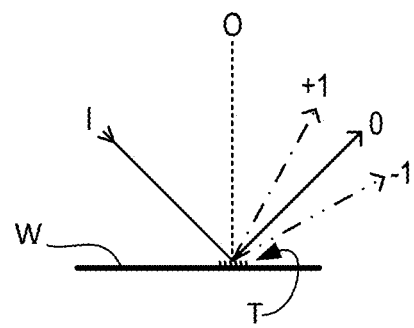

As shown in more detail in FIG. 3(b), target grating T as an example of a target structure is placed with substrate W normal to the optical axis O of objective lens 16. In the case of an off-axis illumination profile, a ray of illumination I impinging on grating T from an angle off the axis O gives rise to a zeroth order ray (solid line O) and two first order rays (dot-chain line +1 and double dot-chain line −1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Referring also to FIG. 3(a), under the first illumination mode with rays 30a, +1 order diffracted rays from the target grating will enter the objective lens 16 and contribute to the image recorded at sensor 23. When the second illumination mode is used, rays 30b are incident at an angle opposite to rays 30a, and so the −1 order diffracted rays enter the objective and contribute to the image. Aperture stop 20 blocks the zeroth order radiation when using off-axis illumination. As described in the prior publications, illumination modes can be defined with off-axis illumination in X and Y directions.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture 20 could be used to pass substantially only one first order of diffracted light to the sensor. In a further example, prisms are used in place of aperture stop 20 which have the effect of diverting the +1 and −1 orders to different locations on sensor 23 so that they can be detected and compared without the need for two sequential image capture steps. This technique is disclosed in the above-mentioned published patent application US2011102753A1, the contents of which are hereby incorporated by reference. 2nd, 3rd and higher order beams (not shown in FIG. 3) can be used in measurements, instead of or in addition to the first order beams. As a further variation, the off-axis illumination mode can be kept constant, while the target itself is rotated 180 degrees beneath objective lens 16 to capture images using the opposite diffraction orders.

The above techniques are typically performed using radiation with a visible wavelength. As such, the scatterometry targets have a pitch that is larger than that of the product structures on the substrate. As an example, a scatterometry target may have a target grating pitch measured in microns (µm), whereas product structures on the same substrate may have a pitch measured in nanometers (nm).

This difference in pitch induces an offset between the measured overlay and the actual overlay on the product structures. The offset is at least partly due to optical projection distortions in the lithographic apparatus and/or different processing in other steps of the manufacturing process. Presently, the offset comprises a significant contribution to the overall measured overlay. Reducing or eliminating it will therefore improve overall overlay performance.

Metrology tools may be developed which use sources that emit radiation in "soft X-ray" or EUV range, for example having wavelengths in the range from 0.1 to 100 nm, or, optionally, in the range from 1 to 50 nm, or optionally, in the wavelength range from 10 to 20 nm. Examples of such sources include Discharge Produced Plasma sources, Laser Produced Plasma Sources or High-order Harmonic Generation (HHG) sources. HHG sources are known to be able to provide large flux of collimated photons (high luminance) in the emitted light.

HHG sources used in metrology applications are illustrated and further described in the European patent applications EP152020301, EP16168237, EP16167512, which are hereby incorporated in their entirety by reference. In metrology applications, such HHG sources may be used (for example) in normal incidence, very close to normal incidence (e.g., within 10 degrees from normal), at a grazing incidence (e.g., within 20 degrees from surface), at an arbitrary angle or at multiple angles (to obtain more measurement information in a single capture).

Figure 4:
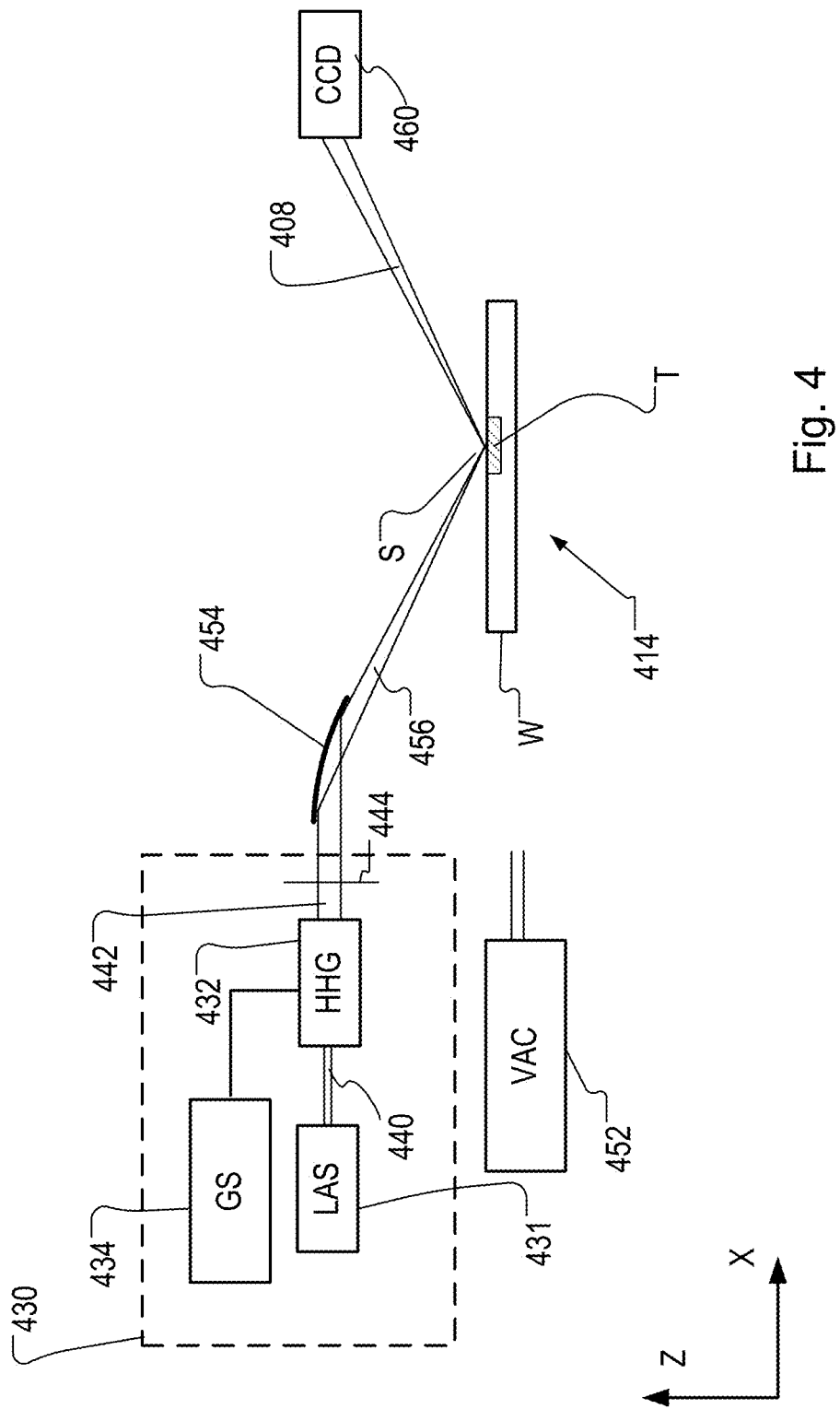
FIG. 4 schematically illustrates a metrology apparatus using a HHG source adaptable according to an embodiment of the invention.

FIG. 4 illustrates a metrology arrangement showing the radiation source 430 in more detail. Radiation source 430 is an HHG source for generating "soft X-ray"/EUV (high harmonic) radiation based on high harmonic generation (HHG) techniques. Main components of the radiation source 430 are a pump radiation source 431 (e.g. a pump laser or oscillator) and an HHG medium, such as a HHG gas cell 432. A gas supply 434 supplies suitable gas to the gas cell, where it is optionally ionized by an electric source (not shown). The pump radiation source 431 may be for example a fiber-based laser with an optical amplifier, producing radiation pulses of infrared radiation lasting less than 1 ns (1 nanosecond) per pulse, with a pulse repetition rate up to several megahertz, as required. The wavelength of the pump radiation may be for example in the region of 1 µm (1 micron). The radiation pulses are delivered as a pump radiation beam 440 to the HHG gas cell 432, where a portion of the radiation is converted to higher frequencies. From the HHG gas cell 432 emerges a beam of measurement radiation 442 including coherent radiation of the desired wavelength or wavelengths.

The measurement radiation 442 may contain multiple wavelengths. If the radiation is also monochromatic, then measurement calculations (reconstruction) may be simplified, but it is easier with HHG to produce radiation with several wavelengths. These are matters of design choice, and may even be selectable options within the same apparatus. Different wavelengths will, for example, provide different levels of contrast when imaging structure of different materials. For inspection of metal structures or silicon structures, for example, different wavelengths may be selected to those used for imaging features of (carbon-based) resist, or for detecting contamination of such different materials.

One or more filtering devices 444 may be provided. For example a filter such as a thin membrane of Aluminum (Al) may serve to cut the fundamental IR radiation from passing further into the inspection apparatus. A grating may be provided to select one or more specific harmonic wavelengths from among those generated in the gas cell 432. Some or all of the beam paths may be contained within a vacuum environment, bearing in mind that EUV radiation is absorbed when traveling in air. The various components of radiation source 430 and illumination optics can be adjustable to implement different metrology 'recipes' within the same apparatus. For example different wavelengths and/or polarization can be made selectable.

From the radiation source 430, the filtered measurement beam enters an inspection chamber where the substrate W including a structure of interest or target structure is held for inspection by substrate support 414. The target structure is labeled T. The atmosphere within inspection chamber is maintained near vacuum by vacuum pump 452, so that the soft X-ray radiation can pass without undue attenuation through the atmosphere. The illumination system includes one or more optical elements 454 for focusing the radiation into a focused beam 456, and may comprise for example a two-dimensionally curved mirror, or a series of one-dimensionally curved mirrors, as described in the prior applications mentioned above. Diffraction gratings such as the spectroscopic gratings can be combined with such mirrors, if desired. The focusing is performed to achieve a round or elliptical spot under 10 µm in diameter, when projected onto the structure of interest. Substrate support 414 comprises for example an X-Y translation stage and a rotation stage, by which any part of the substrate W can be brought to the focal point of beam to in a desired orientation. Thus the radiation spot S is formed on the structure of interest. The radiation scattered 408 from the structure of interest is then detected by detector 460.

Figure 5:
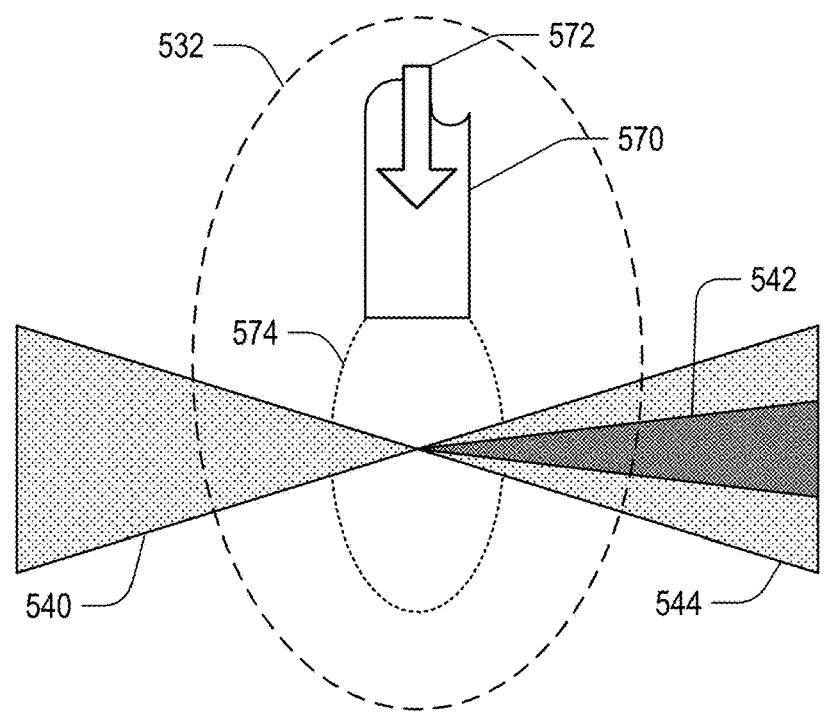
FIG. 5 shows schematically details of a HHG gas cell usable in a HHG source.

FIG. 5 shows a more detailed illustration of an exemplary HHG gas cell, such as may for example be implemented in the system described in FIG. 4. For ease of comparison with FIG. 4, elements of FIG. 5 similar to corresponding elements of FIG. 4 are labelled with reference signs similar to those used in FIG. 4, but with prefix "5" instead of "4".

Shown is the incoming pump radiation 540 (e.g IR radiation), focused on HHG gas cell 532 (or other HHG generating medium). Shown beyond the HHG gas cell 532 is the generated HHG radiation (measurement radiation or soft X-ray/EUV radiation) 542 and the remaining pump radiation 544, which needs to be filtered out of the generated measurement radiation 542. As there is typically a region of overlap of the generated measurement radiation 542 and the remaining pump radiation 544, a filter which is largely transparent to the measurement radiation 542, but which blocks the pump radiation 544 is required. This may in some examples be solved by using ultra-thin metal film filters. Within the HHG gas cell, a capillary tube 570 delivers gas (i.e. the HHG medium) into the inspection chamber (as indicated by arrow 572). Once the gas exits the capillary tube, it spreads into the inspection chamber dependent on a number of characteristics (e.g. velocity, material properties of the fluid and properties of the capillary tube), thereby forming a "cloud" of gas 574. The pump radiation propagates through the gas, thereby generating the measurement radiation. As described above, the inspection chamber is maintained near vacuum to avoid the generated soft X-ray radiation being absorbed by the presence of atmospheric particles.

One problem with the known exemplary arrangement is that gas particles spread substantially in all directions once they exit the capillary tube. While the gas particles are necessary to generate the measurement radiation, as described above, any gas particles present in the path of the measurement radiation will absorb the measurement radiation. As a substantial percentage of the gas particles may propagate along or through the path of the measurement radiation, a substantial portion of the measurement radiation may be absorbed in the known system. In other terms, gas particles in the path of the measurement radiation may negatively affect the intensity and the temporal stability of the measurement radiation.

The inventors have realized that it is possible to provide an apparatus that delivers gas, while minimizing the amount of absorption of the generated radiation.

Figure 6:
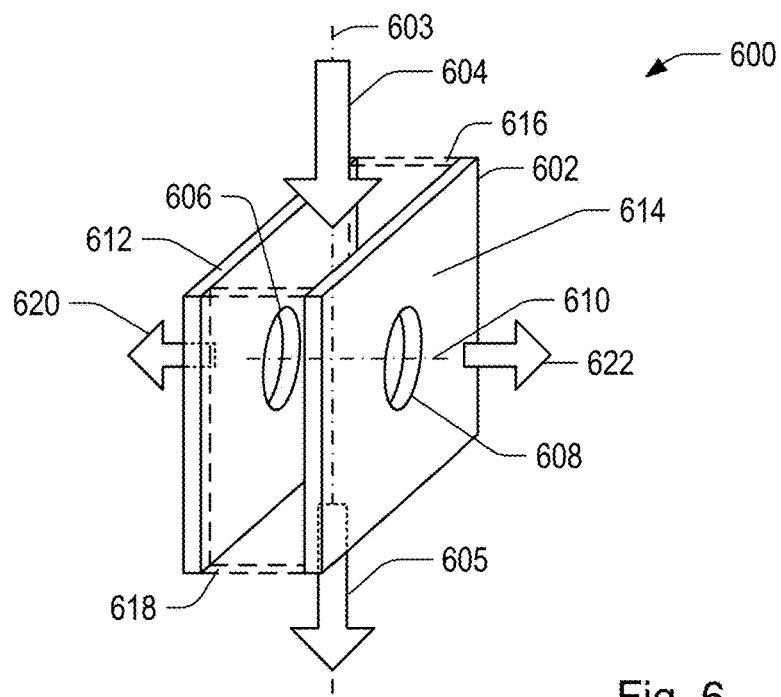
FIG. 6 shows a first exemplary gas delivery element usable in a HHG gas cell.
Figure 7A:
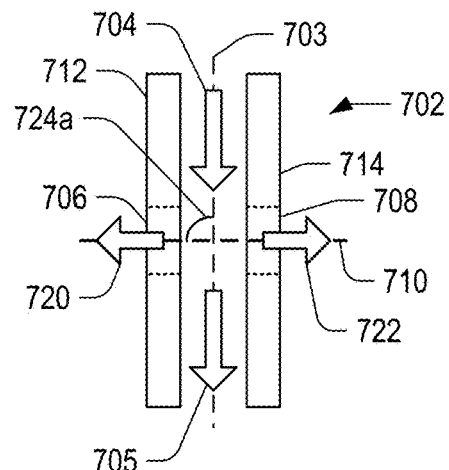
FIGS. 7(a)-7(e) illustrate the principle of the gas delivery element according to the present invention.
Figure 7B:
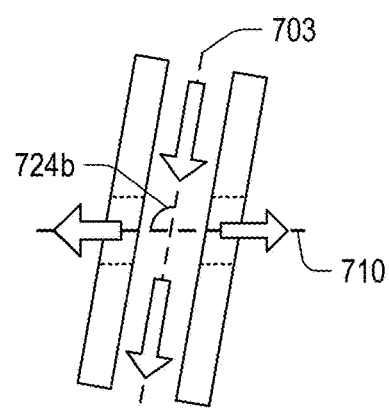
Figure 7C:
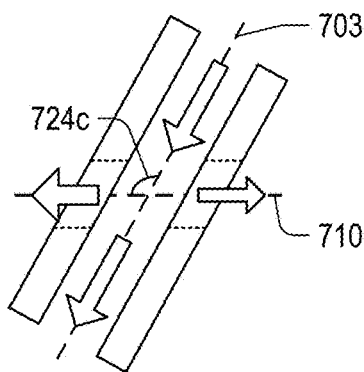
Figure 7D:
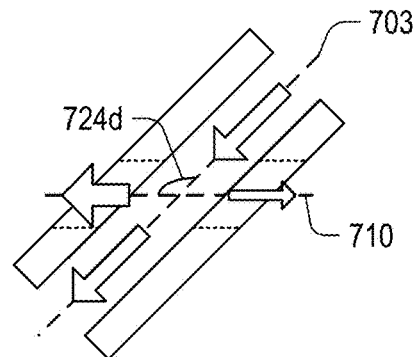
Figure 7E:
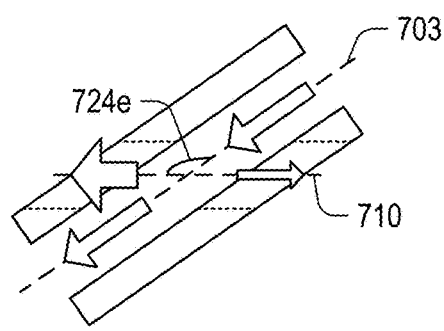

FIG. 6 illustrates a gas delivery system 600 for use in an illumination source in accordance with an aspect of the present invention. The gas delivery system may be implemented in a suitable radiation or illumination system, such as the one shown in FIG. 4 above.

The system comprises a gas delivery element 602 that is arranged to direct gas in at least a first direction 603. The gas delivery element comprises an optical input 606. Additionally, the gas delivery element comprises an optical output 608. The optical input and the optical input define an optical path 610 that is oriented in a second direction, the second direction being non-perpendicular and non-parallel to the first direction. The optical input and/or the optical output may in some examples be dependent on the characteristics of the pump radiation beam. In one example, the optical input and optical output are matched to substantially conform to the beam shape of the pump radiation.

The gas delivery element may have any suitable or convenient shape. In the present examples, the gas delivery element comprises a two pairs of opposed walls; a first wall 612 that comprises the optical input 606; a second wall 614 that comprises the optical output; a first side wall 616; and a second side wall 618.

During operation, gas 604 enters the gas delivery element and flows substantially in the first direction 603. A first portion of the gas 620 will escape through the optical input 606, and a second portion of the gas 622 will escape through the optical output 608. As explained above, the second portion of the gas will serve to absorb the generated radiation, which reduces the intensity of the generated radiation. A third portion 605 of the gas is directed towards an output of the gas delivery element.

The gas delivery system is arranged so that the pump radiation beam propagates along the optical path 610, and so that the pump radiation beam is focused at a point that is substantially inside the gas delivery system (i.e. located on the optical path 610 and between the first wall 612 and the second wall 614). In other terms, the pump radiation beam is arranged so as to maximize the intensity of the pump radiation (i.e. having a focus point or "beam waist") positioned within the gas flow inside the gas delivery element. It will, however, be appreciated that this is for exemplary purposes only. In some examples, the focus point is positioned on the optical path, but is not located inside the gas delivery element. In an example, the focus point is positioned on the input side of the gas delivery element. In another example, the focus point is positioned on the output side of the gas delivery element.

It will, of course, be appreciated that a plurality of specific cross-sections and/or shapes of the gas delivery element may be envisaged. In the present example, the gas delivery element is comprised of two pairs of opposed walls that define a specific cross-section for the gas to flow within. It will be appreciated that a number of specific cross-sections (including, but not limited to: circular; elliptical; or rectangular) may be envisaged. In some examples, the cross-section of the gas delivery element may be adapted to provide one or several specific effect, e.g. specific flow profiles of the gas.

FIG. 7 illustrates schematically the principle of the present invention. For ease of comparison with FIG. 6, elements of FIG. 7 similar to corresponding elements of FIG. 6 are labelled with reference signs similar to those used in FIG. 6, but with prefix "7" instead of "6".

The gas delivery element 702 delivers gas 704 in the first direction 703. In the present example, the gas delivery element is substantially identical to that showed in FIG. 7, i.e. it comprises a first wall 712 having an optical input 706 therein and a second wall 714 having an optical output 708 therein. A first portion of the gas 720 will escape through the optical input 706 and a second portion of the gas 722 will escape through the optical output 708. As explained above, the second portion of the gas will serve to absorb the generated radiation, which reduces the intensity of the generated radiation. A third portion of the gas 705 will propagate towards an output of the gas delivery element.

Turning now specifically to FIG. 7(*a*), which illustrates the known situation, the first direction 703 is perpendicular to the second direction 710, i.e. the angle 724*a* between the first direction and the second direction is 90 degrees. Due to this perpendicularity, the portion of gas escaping from the optical input is substantially identical to the portion of gas escaping from the optical output.

FIG. 7(*b*) illustrates an exemplary situation in accordance with an aspect of the present disclosure. In this exemplary situation, the first direction 703 arranged relative to the second direction 710 at an angle 724*b* that is not perpendicular or parallel. In the exemplary situation of FIG. 7(*b*), similarly to the situation described in FIG. 7(*a*), a first portion of the gas will escape through the optical input and a second portion of the gas will escape through the optical output. Due to the non-perpendicularity, the first portion of gas is larger than the second portion of gas.

FIGS. 7(*c*)-7(*e*) illustrate a number of exemplary situations substantially similar to the one illustrated in FIG. 7(*b*), but for different values of the angle 724*c*, 724*d*, 724*e* between the first direction and the second direction. As will be appreciated, as the angle between the first direction 703 and the second direction 710 increases, the gas flow through the optical input (i.e. the first portion) increases, and the gas flow through the optical output (i.e. the second portion) decreases. It will be appreciated that the values illustrated below are exemplary only so as to illustrate the principles of the present disclosure.

| Angle (degrees) | Flow through optical input (a.u.) | Flow through optical output (a.u.) |
|---|---|---|
| 0 | 1 | 1 |
| 10 | 1.09 | 0.93 |
| 30 | 1.67 | 0.70 |
| 45 | 2.25 | 0.52 |
| 50 | 2.83 | 0.46 |

The increased gas flow on the input side of the gas delivery element does not substantially affect the output of measurement radiation. However, by reducing the amount of gas that exits the gas delivery element through the optical output, the absorption of the soft X-ray radiation due to the presence of particles at the optical output is reduced. In turn, this increases the radiation output of the illumination source.

Figure 8:
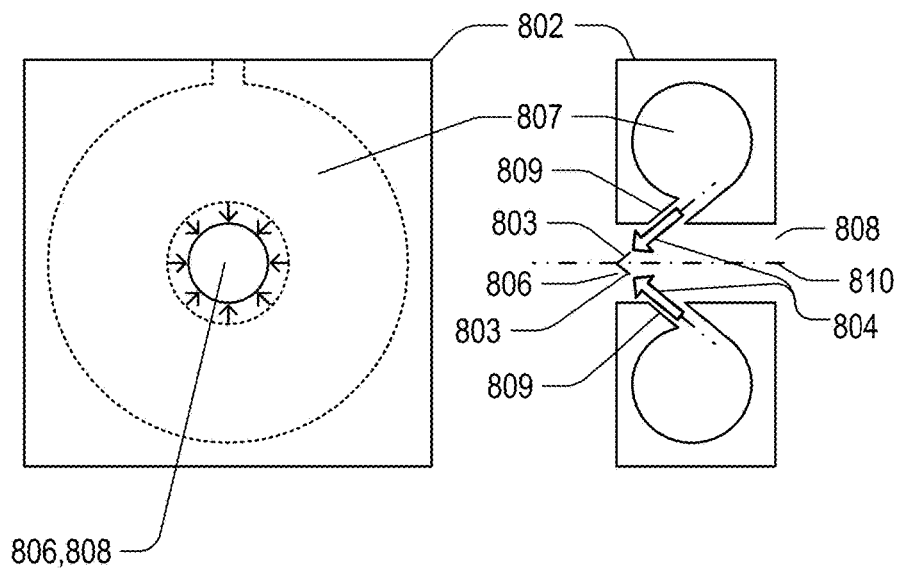
FIG. 8 shows a second exemplary gas delivery element according to the present invention.

FIG. 8 shows a second exemplary implementation of a gas delivery system for use in an illumination source in accordance with a second aspect of the present invention. For ease of comparison with FIG. 6, elements of FIG. 8 similar to corresponding elements of FIG. 6 are labelled with reference signs similar to those used in FIG. 6, but with prefix "8" instead of "6".

Similarly to the example described with reference to FIG. 6 above, the gas delivery element 802 comprises an optical input 806 and an optical output 808 that define an optical path. In the present example, the optical path forms part of a substantially cylindrical radiation guide that defines the second direction 810. The gas delivery element further comprises a substantially toroidal gas delivery component 807. The toroidal gas delivery component is connected to the radiation guide by way of at least one gas delivery passage 809, thereby to deliver gas to the radiation guide in at least a first direction 803. The gas delivery passage may have any suitable shape. In the present example, the gas delivery passage has a substantially frustro-conical shape so that the gas is delivered substantially symmetrically around the second direction 810. In other terms, the gas delivery passage delivers gas 804 at a plurality of angles that are non-perpendicular and non-parallel to the second direction.

It will be appreciated that the implementations discussed above are exemplary only, and that many specific implementations may be envisaged in accordance with the principles of the present disclosure.

As discussed above, it is desirable to maximize the intensity and stability of the measurement radiation. In order to ensure stability, it is necessary to ensure that the supply of gas to the HHG gas cell is kept at a substantially constant level. Any variation or instability of the characteristics of the supplied gas, e.g. (but not limited to) gas flow speed or gas flow volume, will cause the characteristics of the measurement radiation to vary over time. For example, a reduced flow of gas will reduce the amount of measurement radiation, which reduces the perceived intensity of the measurement radiation. This, in turn, may influence the quality of the measurements performed using the measurement radiation.

Accordingly, it is advantageous maintain the stability of the gas supplied to the HHG gas cell at a constant and high level. A number of exemplary implementations will now be discussed that are intended to improve the stability of gas supply to the gas delivery system.

Figure 9:
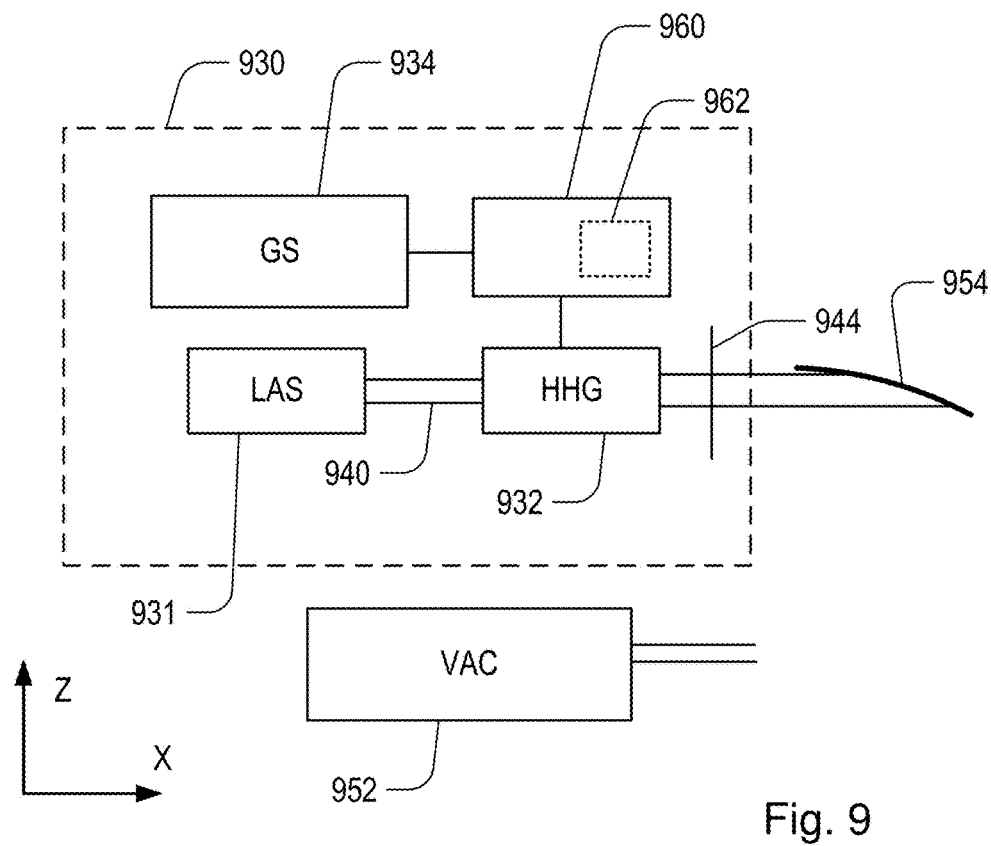
FIG. 9 shows a HHG radiation source according to an embodiment of the present invention.

FIG. 9 illustrates a radiation source 930 comprising an exemplary gas delivery system. For ease of comparison with FIG. 4, elements of FIG. 9 similar to corresponding elements of FIG. 4 are labelled with reference signs similar to those used in FIG. 4, but with prefix "9" instead of "4".

The gas delivery system comprises a gas buffer element 960 that is positioned between the gas source 934 and the HHG gas cell 932. The gas buffer element has an input that is connected to an output of the gas source, and an output that is connected to an input of the HHG gas cell. In operation, gas is transferred from the gas source (which may be a high pressure gas bottle fitted with a simple valve) and into the gas buffer element. Typically, gas sources comprise outputs that have high levels of gas flow variation and instability. The gas buffer element is operable to absorb variations in gas flow from the gas source and to deliver a substantially constant gas flow to the HHG gas cell.

The gas buffer element may have any suitable shape or form. In some examples, it may be provided with control means 962 for controlling one or more of the characteristics of the gas. In specific examples, the gas buffer element comprises a temperature control element. This allows the gas temperature to be controlled, which may reduce the variations of the specific mass of the gas due to temperature variations of the environment at the gas delivery system itself. It will be appreciated that, while discussed as being comprised as part of the gas buffer element in the present example, the temperature control element may be positioned outside, whilst being used in conjunction with, the gas buffer element in some examples. In other examples, additional or alternative control means may be provided. In some examples, the gas buffer element or gas delivery system may comprise a gas composition control element. This is particular relevant in situations where the gas comprises a mixture of specific gasses or compounds. In yet other examples, the gas buffer element or gas delivery system may comprise a purity control element. This is relevant in situations where quality or purity control of the gas is a concern. In specific examples, the purity control element is coupled to a scrubber or gas replacement element.

FIG. 10 schematically illustrates a number of exemplary gas delivery elements for improving the flow profile of the gas. For ease of comparison with FIG. 6, elements of FIG. 10 similar to corresponding elements of FIG. 6 are labelled with reference signs similar to those used in FIG. 6, but with prefix "10" instead of "6".

FIG. 10(a) shows a known gas delivery element 1002, e.g. a capillary tube such as discussed with reference to FIG. 5. It is known that, in a gas delivery element such as the one shown, a moving gas 1004 has a specific flow profile (as illustrated by the dotted line 1024). Typically, the velocity and pressure of the gas is largest near the middle of the gas delivery element and is smallest near the walls of the gas delivery element. At the output of the gas delivery element, the flow profile 1026a is substantially identical to that within the gas delivery element. Since the flow profile is not transversally homogenous, the gas spread on exiting the gas delivery is higher than it would be if the gas flow profile is substantially transversally homogenous (e.g. if the gas flow in the gas delivery element is laminar). As a result, a "cloud" of gas is formed in the area wherein the gas interacts with incoming pump radiation. In order to maximize conversion of pump radiation into generated radiation and order to minimize the absorption of the measurement radiation by gas particles, it is desirable to ensure that the gas glow is laminar.

FIG. 10(b) illustrates an exemplary gas delivery element 1002 in accordance with the present disclosure. It will be appreciated that, while illustrated as a capillary tube substantially identical to the one shown in FIG. 10(a), the principles of this example may be applied to any number of specific implementations.

The gas delivery element shown in FIG. 10(b) comprises a filtering element 1028. The filtering element is operable to modify the flow profile of the gas flowing through the gas delivery element. In some examples, the filtering element is operable to provide gas with a laminar flow profile 1026b at the output of the gas delivery element. By reducing the amount of turbulence in the gas, the spread of gas once it exits the gas delivery element is reduced. This, in turn, maintains a higher concentration of gas in the area wherein the gas interacts with the pump radiation (which increases the conversion efficiency and the resulting intensity of the generated radiation). In the present example, the filtering element 1028 comprises a first filter component 1030 and a second filter component 1032. In this example, both the first filter component and the second filter component comprise a plurality of pores. The first filter component equalizes the pressure and velocity of the gas inside the filtering element. The second filter provides a uniform flow distribution of the gas exiting the gas delivery element. It will be appreciated that it is possible to control the specific flow distribution by controlling the pore size and distribution of the gas, for example to optimize the generation of measurement radiation. It will further be appreciated that this example is exemplary only, and that a number of specific implementations may be envisaged that perform the required function, i.e. providing a laminar flow of fluid in the gas delivery element. It will further be appreciated that, while illustrated in FIG. 10 as a capillary tube, the principles of this example may be readily applied to other specific exemplary implementations of the present disclosure.

To generate (e.g., soft X-ray) measurement radiation with a reasonable energy conversion efficiency, several physical parameters can be tuned. One such parameter which has an impact on generation of HHG measurement radiation is the number density of the gas within the gas cell. Preferably, the number density should be high within a pump radiation interaction region (where pump radiation interacts with/excites the gas) for phase matching and ionization, but low in the region immediately beyond this location to prevent measurement radiation absorption. Furthermore, for efficient measurement radiation generation, the high density region should extend over a certain minimum distance, e.g., a few millimeters, and then drop off sharply to a low density, e.g., within 10% of the length of the pump radiation interaction region along the direction of the pump radiation beam.

It is therefore proposed to use a gas jet shaping device to shape the gas jet such that the drop-off length from high number density to low number density is decreased. The gas jet shaping device may further shape the gas jet such that length of the pump radiation interaction region (length of region with high number density) is increased relative to there being no gas jet shaping device present. In an embodiment, gas jet shaping device may be such that the short drop off length is less than 10% of the length of the pump radiation interaction region. "Low density" in this context may comprise the background pressure in the vacuum vessel, which should be sufficiently low so as to not absorb significant amount of the measurement radiation, e.g., typically 1-10 Pa. In an embodiment, the drop off length may describe the distance over which the gas density drops by at least a factor of ten, from the density at the pump radiation interaction region to the low density region. The actual length of the pump radiation interaction region may be varied by an order of magnitude or more; the optimal length of the pump radiation interaction region will depend on gas type and pump radiation beam intensity and focus.

In an embodiment, the gas jet shaping element may comprise an angled wall element located below the gas delivery element. The angled wall element may be attached to the gas delivery element at a point adjacent its output (e.g., the nozzle output) such that it extends below this output (for example, by a few mm—e.g., less than 10 mm) at an angle towards the emitted gas jet. The angle (relative to the vertical or z-axis) may be, for example, between 20 and 60 degrees, between 20 and 50 degrees, or between 30 and 40 degrees. In an embodiment, the gas jet shaping element may comprise an angled horizontal-cylindrical-segment (e.g., a cylindrical segment cut horizontally), open at its bottom end. More specifically, the gas jet shaping element may comprise a semi-cylindrical element. The gas jet shaping element may be located such that a wall of the gas jet shaping element is located between the gas jet and optical output of the gas cell, and no wall of the gas jet shaping element is located between the gas jet and optical input of the gas cell. The gas shaping element may comprise an aperture to transmit the generated measurement radiation.

FIG. 11 is a schematic illustration of a gas delivery element 1170 with gas jet shaping element 1180 according to an embodiment, depicted (a) in isometric projection and (b) in cross-section. The gas delivery element 1170 comprises nozzle outlet 1184. The gas jet shaping element 1180 in this embodiment is semi-cylindrical, with its wall located between the gas jet 1104 and optical outlet (not shown). The gas shaping element 1180 comprises an aperture 1182 to transmit the generated measurement radiation. The shape and location of the gas shaping element 1180 results in a sharp drop-off in the number density of the gas jet 1104, indicated by dotted line 1186. As such, the region along the optical path, immediately after this dotted line 1186 in the direction towards the optical outlet, has a very low number density (e.g., background pressure in the vacuum vessel). This acts to reduce the absorption of the generated measurement radiation by the gas jet 1104. Relatively few gas molecules go through aperture 1182 due to the high speed and kinetic energy of the gas molecules in the vertical direction.

In an embodiment, the wall of gas jet shaping element 1180 may be thin, for example less than 0.2 mm, or in the region of 0.1 mm. It may comprise any suitable material, e.g., a weldable material (e.g., so that it can be welded to a disc 1187 around the nozzle outlet 1184). The material may be wear resistant and have a high melting temperature. Suitable materials may comprise tungsten, molybdenum, aluminum or stainless steel, for example.

The effect of the gas jet shaping element 1180 is to provide for a higher density gas on the gas delivery side of the gas jet shaping element 1180, and a steep density drop off at the outlet side of the gas jet shaping element 1180, close to the location of aperture 1182. More specifically, the gas jet shaping element 1180 provides for a relatively longer (relative to there being no gas jet shaping element) pump radiation interaction region on its gas delivery side and a density drop off region having a length less than 10% the length of the pump radiation interaction region on its outlet side.

Figure 12:
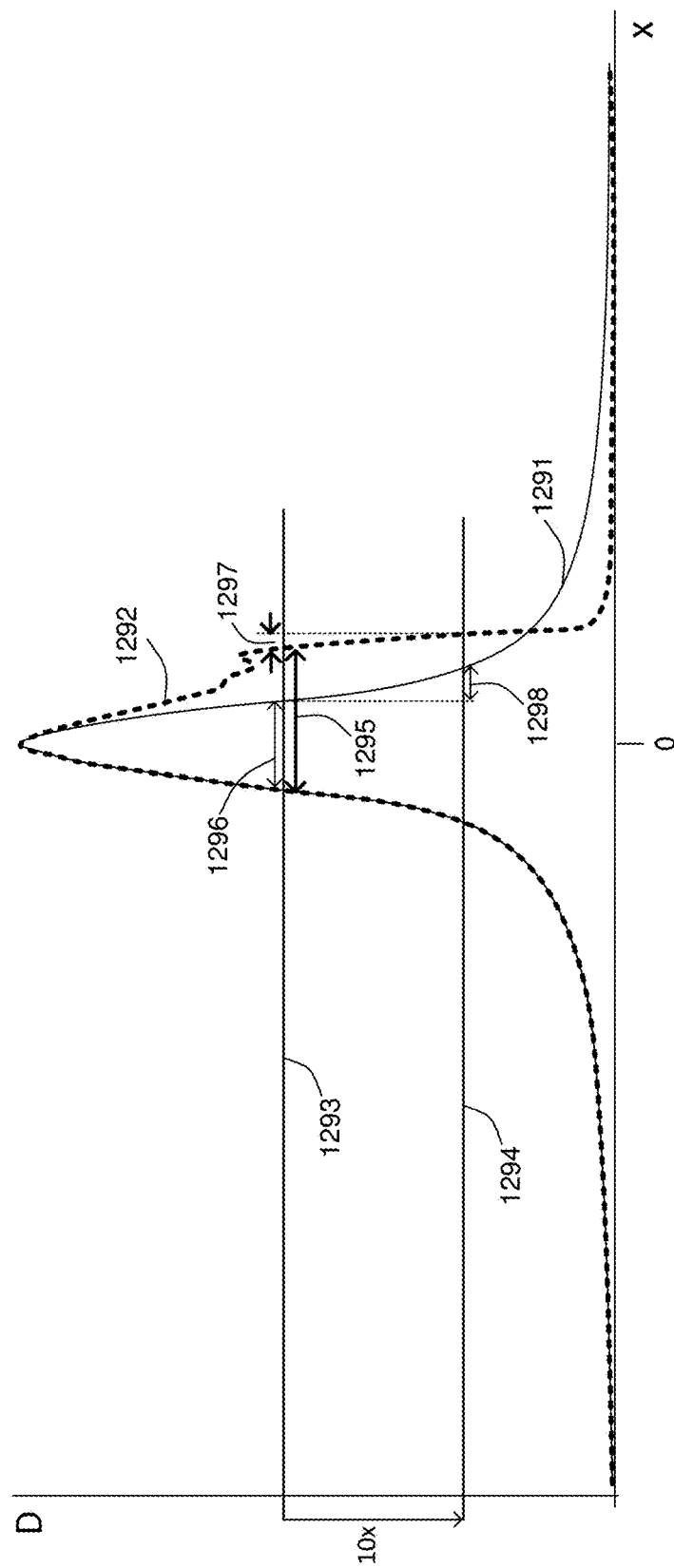
FIG. 12 is a plot of number density of the emitted gas against distance along the optical path for the gas delivery element of FIG. 11 and a gas delivery element without a gas jet shaping device.
Figure 13A:
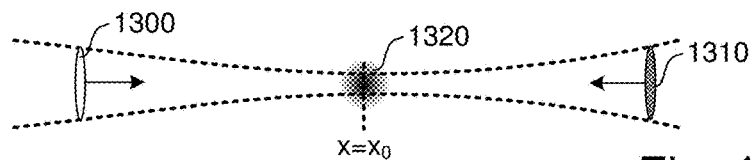
FIGS. 13(a)-13(d) show schematically, four steps of a method for generating soft X-ray measurement radiation using a plasma to mitigate reabsorption.
Figure 13B:
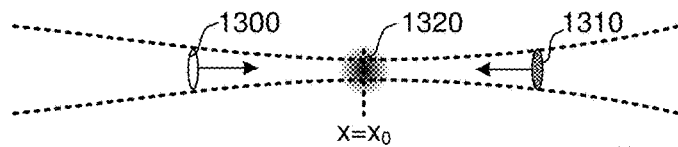
Figure 13C:
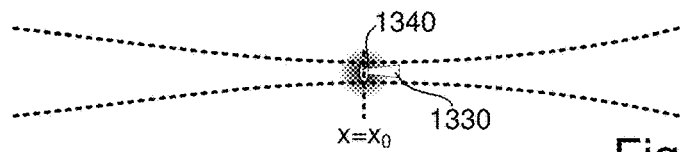
Figure 13D:
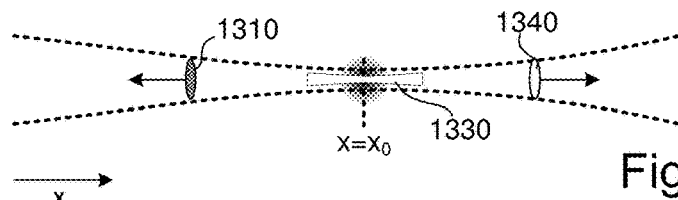

FIG. 12 illustrates this effect. It shows two gas density profiles, first gas density profile 1291 (solid line) for a gas delivery system having no gas shaping element, and a second gas density profile 1292 (dotted line) for a gas delivery system having a gas shaping element as disclosed herein. In each case the gas density profile comprises a plot of molecular gas density on a logarithmic scale (on the y-axis) against distance along the optical path (x-axis) with the origin 0 at the center of the output nozzle. Also marked on the y-axis is a first gas density level line 1293 indicating a first gas density level at which the pump radiation will excite the gas. This corresponds to a region of relatively high density (e.g., at least 50% of peak) at a particular distance below the nozzle output; the pump radiation does not go through the density peak since the laser interaction length would then be zero. A second gas density level line 1294 indicates the gas density level at which the gas density falls by an order of magnitude (i.e., a factor of 10) relative to the first gas density level. The second gas density profile 1292 shows a longer pump radiation interaction length 1295 relative to the pump radiation interaction length 1296 of the first gas density profile 1291. Also shown is the drop off length 1297 of the second gas density profile 1292 and the drop off length 1298 of the first gas density profile 1291. Of particular note is that the gas density drop off length 1297 is less than 10% of the pump radiation interaction length 1295 for the second gas density profile 1292, while the gas density drop off length 1298 is greater than 10% of the pump radiation interaction length 1296 for the first gas density profile 1291.

It should be noted that the actual length of the pump radiation interaction region 1295 is variable depending on gas type, pressure etc. As such, one purely exemplary operation point may have a pump radiation interaction length 1295 of 1.5 mm and a drop off length 1297 of 0.1 mm. However this can, for example, also be scaled to be 10× smaller, with a higher gas density. Hence another (purely exemplary) operation point may have a pump radiation interaction length 1295 of 0.2 mm and a drop off length 1297 of <0.02 mm. The gas density profile is scalable in width (x-axis: mm) and height (y-axis: gas density).

It should be noted that the gas jet shaping element as disclosed herein may be used in conjunction with the other embodiments disclosed, i.e., a gas delivery element with an optical path which is non-perpendicular or non-parallel to the gas jet delivery direction, or it can be incorporated in a more conventional gas delivery element where the optical path is perpendicular to the gas jet delivery direction.

As already described, there are advantages in reducing the gas density drop off length. Reabsorption by the gas of the generated measurement radiation may be prevented substantially where the gas density drop off of the gas medium has a sharp edge in the propagation direction x of the pump radiation, such that the gas density drops off very sharply immediately after the pump radiation interaction length. More specifically, such a sharp edge may be at a position $x=x0$ along the propagation axis x of the pump radiation beam at which the gas density sharply drops from the specific phase-matched density at $x<x0$ to a density at $x>x0$ which is sufficiently low for the gas to be essentially transparent for soft X-ray radiation. The soft X-ray radiation intensity typically reaches a high peak value near the focus of the pump radiation beam. Should the gas density profile slowly drop following this maximum (as is typical), the soft X-ray intensity will decrease to a low value due to its absorption by the gas in the region x>x0. In contrast, where the gas density has a sharp edge near x=x0, absorption in the region x>x0 is substantially avoided and the soft X-ray intensity remains high in the region x>x0. The degree of 'sharpness' of the gas density profile results in this desired behavior when the density drops over a length that is comparable to or smaller than the absorption length of the gas, which is a characteristic length scale dependent on the gas species. Typically, absorption lengths of gases that are suitable for soft X-ray generation at wavelengths below 20 nm are on the order of some tenths of millimeters or smaller. The gas density is typically in the range 1023-1026 m−3.

It is proposed to use a second high intensity (e.g., laser) radiation pulse to generate a highly or fully ionized plasma in the region x>x0 at the moment in time that the soft X-ray pulse passes this region. A plasma is comprised of ions which have a much smaller cross-section for absorption than the original atoms (or molecules) of the gas phase, and therefore will absorb significantly less soft X-ray measurement radiation. This avoids the need for a steep particle density gradient and provides additional control over the exact region in which the measurement radiation is generated and re-absorbed.

A laser intensity of typically ≥1018 W/m2 may be used to generate a highly ionized plasma. To generate this over a length of approximately 3 mm (the length over which the gas density drops significantly in a gas jet configuration) a laser pulse with a wavelength of e.g. 1 μm could be used, focused to a spot of approximately 30 μm diameter. To reach the intensity of 1018 W/m2, the energy of a 50 fs laser pulse would be of the order 0.5 mJ, which is comparable to the pump laser pulse for generating the measurement radiation.

FIG. 13 shows a possible configuration comprising a counter-propagating laser pulse, which illustrates (a)-(d) the pump radiation pulse 1300 and counter-propagating ionization radiation pulse 1310 at different times during the measurement radiation generation process. FIG. 13(a) shows the pump radiation pulse 1300 and ionization radiation pulse 1310 at a first time, each propagating towards the gas target 1320 at x=x0. FIG. 13(b) shows the pump radiation pulse 1300 and ionization radiation pulse 1310 at a later time, each getting nearer to the focus with increased intensity. FIG. 13(c) shows the plasma 1330 being generated as a result of the ionization radiation pulse ionizing the gas target 1320 in the region immediately after x=x0 relative to the pump radiation propagation direction (e.g., x>x0). The delay between the pulses is tuned such that they achieve overlap at (close to) x=x0, the position where the generated measurement radiation intensity reaches its maximum. The generated soft X-ray measurement radiation 1340 therefore propagates through plasma 1330, rather than neutral gas. FIG. 13(d) shows the generated soft X-ray measurement radiation 1340 co-propagating with the pump radiation, subsequent to having propagated through plasma 1330.

The ionization radiation pulse can be synchronized with the pump radiation pulse. This will be automatically the case if the ionization radiation pulse is generated from the same oscillator (e.g., pump laser) as the pump radiation pulse. The delay of the ionization radiation pulse may be tuned such that the plasma is formed at the moment the pump radiation pulse arrives at x=x0 to generate the measurement radiation. The skilled person will recognize that this is reasonably straightforward to achieve with a micrometer and sub-picosecond precision. Accurate timing also means that the position at which the measurement radiation pulses encounter the gas/plasma boundary can be actively chosen. The counter-propagating ionization pulse can be of the same wavelength as the pump laser pulse, or another wavelength. The focus size (and therefore the divergence) of the ionization radiation pulse may be similar, but not necessarily the same, as that of the pump radiation pulse. The focus size and divergence of the ionization radiation can be matched to the size of the generated measurement radiation beam, so that the measurement radiation beam propagates through the highly ionized plasma, instead of the non-ionized gas.

Figure 14:
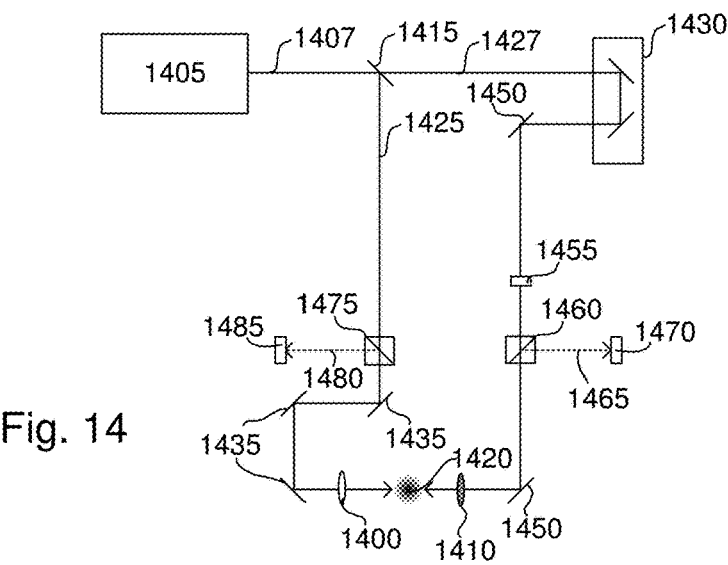
FIG. 14 shows an arrangement for performing the method shown in FIG. 13.

FIG. 14 shows a possible arrangement for generating the counter-propagating pump radiation pulse 1400 and ionization radiation pulse 1410 from a single radiation source (oscillator) 1405. The output radiation 1407 is split by beamsplitter 1415 into pump radiation beam path 1425 and ionization radiation beam path 1427. The pump radiation is directed to the gas target 1420 by optical elements 1435. The ionization radiation is directed to the gas target 1420 by optical elements 1450 and via delay stage 1430. While the delay stage 1430 is shown here in the ionization radiation beam path 1427, it can be located in either beam path, or even both beam paths.

To ensure that the returning ionization radiation pulse is prevented from re-entering the laser source system 1405, a number of ways of separating the laser pulses is possible. Shown here is an arrangement which uses polarization to separate the pulses. A half-wave plate 1455 is located in one of the beam paths (it does not matter which), followed by polarizing beamsplitters 1460, 1475 and beam dumps 1470, 1485 in each beam path. Due to this arrangement, the two pulses 1400, 1410 will have orthogonal polarization, and therefore the incoming radiation pulses can be separated from the returning radiation pulses by means of the polarizing beamsplitters 1460, 1475, with the incoming pulses directed to the beam dumps 1470, 1485. Alternatively, the ionization radiation pulses may be introduced into the system at a slight angle, to separate the beam path of the returning pulses from the beam path of the incoming pulses. As another alternative, different wavelengths may be used for the pulses, which allows separation by dichroic mirrors, or filters.

Figure 15A:
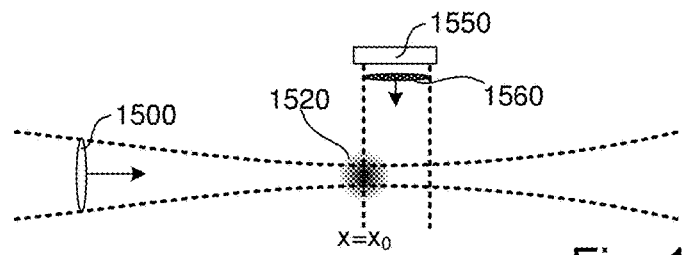
FIGS. 15(a)-15(c) show schematically, three steps of an alternative method for generating soft X-ray measurement radiation using a plasma to mitigate reabsorption.
Figure 15B:
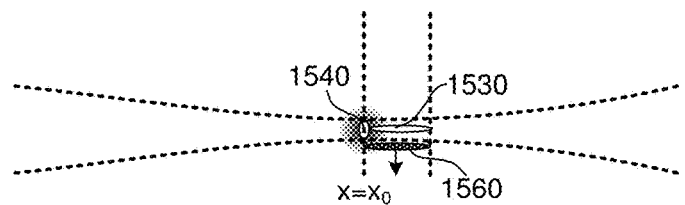
Figure 15C:
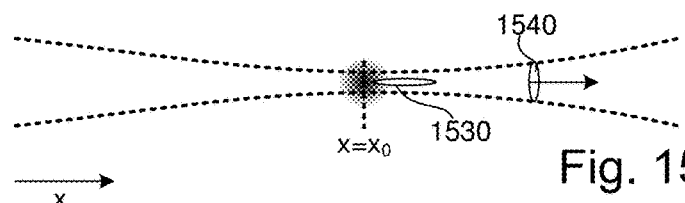

FIG. 15(a)-(c) shows, at three different times, an alternative possible configuration for generating the plasma. This uses a cylindrical lens 1550, cylindrical mirror or other suitable optical element to focus the ionization radiation pulse 1560 into a line focus. This line is oriented on the path of the measurement radiation pulses 1540, (e.g., in the region immediately after x=x0 relative to the pump radiation pulse 1500 propagation direction) such that the generated measurement radiation pulses propagate through plasma 1530 instead of neutral gas atoms. An advantage of this configuration is that a longer plasma can be generated, relative to the FIG. 13 arrangement. Also, there is a greater de-coupling of timing from position. The plasma can be generated at a time (in the order of picoseconds, up to nanoseconds) before the measurement radiation pulses arrive. This avoids the need for accurate timing.

It is not necessary that the ionization radiation pulse arrives from either the opposite direction or an orthogonal direction, relative to the propagation direction of the pump radiation pulse, as is specifically shown in FIGS. 13 and 15. In other embodiments the propagation directions of the ionization radiation pulse and pump radiation pulse may be separated by a different angle. What is relevant is that the generated plasma is adjacent to the area where the generated measurement radiation pulses are generated and such that these measurement radiation pulses have (at most) only a short distance to propagate through the high harmonic generation gas before encountering the plasma.

A further advantage of the plasma generation methods disclosed above is in dose control. By accurately timing the ionization radiation pulse with respect to the pump radiation pulse, and/or by controlling the intensity of the ionization radiation pulse, it is possible to increase or decrease the absorption by the neutral gas. As such, the proposed illumination source may comprise a dose control which controls the timing the ionization radiation pulse with respect to the pump radiation pulse, and/or by controlling the intensity of the ionization radiation pulse. This dose control can also be used to control the dose level and/or effectively temporarily 'switch off' the measurement radiation pulses by ensuring that no plasma is produced. If no plasma is produced and the gas configuration is chosen appropriately, all or nearly all measurement radiation will be reabsorbed by the gas. The dose control can be implemented in any suitable manner, e.g., by suitable software running on a processor which controls the ionization radiation pulse and generation thereof. Such a processor may be a processor which controls operation of the illumination source more generally.

The plasma generated by the ionization radiation source will refract the pump radiation pulse whereas the measurement radiation pulse is only negligibly affected. This is because the frequency of the measurement radiation pulse is much higher than the plasma frequency in the relevant typical density range. This means that it will be easier to separate the pump radiation pulses from the soft X-ray measurement radiation, e.g., by means of a small pinhole in the beam path aligned with the measurement radiation beam but which blocks the refracted, and therefore deflected, pump radiation pulse.

It should be noted that the gas ionization method as disclosed herein may be used in conjunction with the other embodiments disclosed, i.e., a gas delivery element with an optical path which is non-perpendicular or non-parallel to the gas jet delivery direction, and/or gas jet shaping element delivery element as shown in FIG. 11 and/or the provision of two or more gas nozzles described below.

Figure 16A:
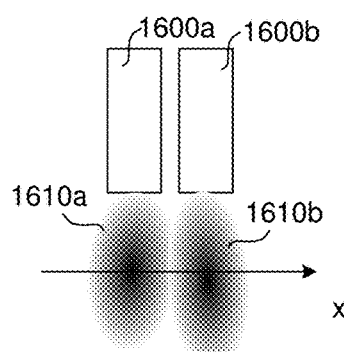
FIGS. 16(a) and 16(b) show (a) a further arrangement for mitigating reabsorption of generated measurement radiation; and (b) a plot of gas density against the pump radiation propagation direction x, illustrating the working principle behind the arrangement of FIG. 16(a).

FIG. 16 illustrates an alternative arrangement for mitigating for the reabsorption of the measurement radiation by the gas from which it is generated. In this arrangement, it is proposed to use a at least two gas jets with two different gases (e.g., different gas species). FIG. 16(a) illustrates such an arrangement, with first gas nozzle 1600a and second gas nozzle 1600b. The gases can be chosen so that the first gas jet 1610a emitted by the first gas nozzle 1600a comprises the gas medium which efficiently produces the desired (e.g., soft X-ray) measurement radiation. As such, this first gas may be the gas used in the other embodiments described above. A second gas jet 1610b emitted by the second gas jet nozzle 1600b may comprise a second gas which has a much lower absorption at the desired (e.g., soft X-ray) wavelength. For example, if the measurement radiation generated comprises soft X-ray radiation in the 10-20 nm range, then neon may be a suitable first gas and argon may be a suitable second gas. Argon has a much lower absorption at that wavelength range than neon.

Figure 16B:
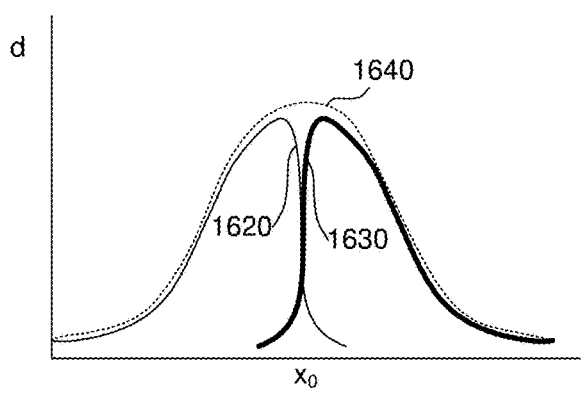

The second gas jet 1610b flow acts to shape the first gas jet 1610a to obtain a steep density drop off gradient immediately after the x=x0 position. This is illustrated in FIG. 16(b), which is a plot of gas density against distance in x (pump radiation propagation direction). The first plot 1620 (thinner line) is the density profile for the first gas and the second plot 1630 (thicker line) is the density profile for the second gas. Also shown (dotted line) is a plot of the overall gas density 1640 within the gas target region (HHG gas cell). It can be seen that the density profile 1620 for the first gas shows a very steep drop-off at the x=x0 position. Beyond this position is essentially only the second gas which will not absorb the measurement radiation.

In the embodiment shown in FIG. 16(a) the gas jets are adjacent each other. Optionally, the second gas jet 1610b may be tilted towards the first gas jet 1610a. In another possible embodiment, the gas jets may be arranged concentrically; e.g., with the first gas nozzle located inside the second gas nozzle.

More gas jets, having different gas profiles may be added to shape the gas profile of the first gas. The gas jets can be operated at similar or at different gas pressures. They can also be of different shape and size.

It should be noted that the two or more gas nozzles embodiment as disclosed herein may be used in conjunction with the other embodiments disclosed, i.e., a gas delivery element with an optical path which is non-perpendicular or non-parallel to the gas jet delivery direction, and/or gas jet shaping element delivery element as shown in FIG. 11 and/or the ionization pluses to generate a plasma method described above.

Further embodiments are defined in the subsequent numbered clauses:

1. A gas delivery system for use in an illumination source, comprising a gas delivery element arranged to direct gas in at least a first direction, wherein the gas delivery element comprises:
   an optical input; and
   an optical output,
   wherein the input and the output define an optical path, the optical path being oriented in a second direction, and
   wherein the second direction is non-perpendicular and non-parallel to the first direction.

2. A gas delivery system according to claim 1, wherein the first direction is at an obtuse angle relative to the second direction.

3. A gas delivery system according to claim 1 or 2, wherein the optical input and optical output are arranged to allow pump radiation to pass through the gas to generate high harmonic radiation.

4. A gas delivery system according to claim 3, wherein the optical input and optical input are arranged concentrically with the optical path.

5. A gas delivery system according to claim 3 or 4, wherein the optical input comprises an opening in a first wall of the gas delivery system, and wherein the optical output comprises an opening in an opposing wall of the gas delivery system.

6. A gas delivery system according to any preceding claim, wherein at least one of the optical input or the optical output has a cross section corresponding substantially to a beam cross section of the pump radiation.

7. A gas delivery system according to any preceding claim, further comprising at least one pumping element connected to the gas delivery element.

8. A gas delivery system according to any preceding claim, wherein the gas delivery element has a cross-section in the first direction that is one of: rectangular; circular; or ellipsoidal.

9. A gas delivery system according to any of claims 1 to 7, wherein the gas delivery element comprises a toroidal gas delivery component, the toroidal gas delivery component being arranged to deliver gas to the optical path in at least the first direction.

10. A gas delivery system according to claim 9, wherein the toroidal gas delivery component is arranged to deliver gas to the optical in a plurality of first directions.

11. A gas delivery system according to any preceding claim, further comprising a gas buffer element.

12. A gas delivery system according to claim 11, wherein the gas buffer element comprises a temperature controlling element.

13. A gas delivery system according to any preceding claim, further comprising a filtering element operable to modify a flow profile of the gas.

14. A gas delivery system according to claim 13, wherein the filtering element is operable to provide a laminar flow profile of the gas.

15. A gas delivery system according to any preceding claim, further comprising a gas jet shaping device operable to modify a flow profile of the gas such that number density of the gas falls sharply in the direction of the optical output, after a pump radiation interaction region where pump radiation interacts with said gas.

16. A gas delivery system according to claim 15, wherein the number density of the gas falls by at least a factor of 10 relative to that of the pump radiation interaction region within a drop off region immediately after the pump radiation interaction region in the direction toward said output, a length of said drop off region being 10% or smaller than a length of the pump radiation interaction region.

17. A gas delivery system according to claim 15 or 16, wherein said modification of the flow profile is further operable to extend a length of the pump radiation interaction region relative to there being no gas jet shaping device present.

18. A gas delivery system according to claim 17, wherein said length of the pump radiation interaction region is extended by more than 50% relative to there being no gas jet shaping device present.

19. A gas delivery system according to any of claims 15 to 18, wherein the gas jet shaping device comprises an angled wall element located below the gas delivery element and obtusely angled relative to said first direction.

20. A gas delivery system according to claim 19, wherein the angled wall element is attached at a point adjacent a gas output of the gas delivery element such that it extends below this gas output and at an angle towards the gas emitted.

21. A gas delivery system according to claim 20, wherein the gas jet shaping element comprises an angled horizontal-cylindrical-segment open at its bottom end.

22. A gas delivery system according to claim 21, wherein the gas jet shaping element comprises a semi-cylindrical element.

23. A gas delivery system according to any of claims 19 to 22, wherein the gas jet shaping element is located such that a wall of the gas jet shaping element is located between the pump radiation interaction region and the optical output, and no wall of the gas jet shaping element is located between the gas pump radiation interaction region and the optical input.

24. A gas delivery system according to claim 23, wherein the gas shaping element comprises an aperture in said wall to pass the generated measurement radiation to said optical output.

25. A gas delivery system for use in an illumination source, comprising:
a gas delivery element arranged to direct gas in at least a first direction, wherein the gas delivery element comprises:
an optical input and an optical output together defining an optical path, the optical path being oriented in a second direction; and
a gas jet shaping device operable to modify a flow profile of the gas such that number density of the gas falls sharply in the direction of the optical output after a pump radiation interaction region where pump radiation interacts with said gas.

26. A gas delivery system according to claim 25, wherein the number density of the gas falls by at least a factor of 10 relative to that of the pump radiation interaction region within a drop off region immediately after the pump radiation interaction region in the direction toward said output, a length of said drop off region being 10% or smaller than a length of the pump radiation interaction region.

27. A gas delivery system according to claim 25 or 26, wherein said modification of the flow profile is further operable to extend a length of the pump radiation interaction region relative to there being no gas jet shaping device present.

28. A gas delivery system according to claim 27, wherein said length of the pump radiation interaction region is extended by more than 50% relative to there being no gas jet shaping device present.

29. A gas delivery system according to any of claims 25 to 28, wherein the gas jet shaping device comprises an angled wall element located below the gas delivery element and obtusely angled relative to said first direction.

30. A gas delivery system according to claim 29, wherein the angled wall element is attached at a point adjacent a gas output of the gas delivery element such that it extends below this gas output and at an angle towards the gas emitted.

31. A gas delivery system according to claim 30, wherein the gas jet shaping element comprises an angled horizontal-cylindrical-segment open at its bottom end.

32. A gas delivery system according to claim 31, wherein the gas jet shaping element comprises a semi-cylindrical element.

33. A gas delivery system according to any of claims 29 to 32, wherein the gas jet shaping element is located such that a wall of the gas jet shaping element is located between the pump radiation interaction region and the optical output, and no wall of the gas jet shaping element is located between the gas pump radiation interaction region and the optical input.

34. A gas delivery system according to claim 33, wherein the gas shaping element comprises an aperture in said wall to pass the generated measurement radiation to said optical output.

35. An illumination source for generating high harmonic radiation, comprising:
a pump radiation source operable to emit pump radiation; and
a gas delivery system as claimed in any of claims 1 to 34 or 39 to 43, operable to receive the emitted pump radiation and to generate said high harmonic radiation.

36. An inspection apparatus for measuring a target structure on a substrate, comprising:
an illumination source as claimed in claim 35 for generating high harmonic radiation; and
a sensing element for receiving high harmonic radiation scattered by the target structure.

37. A lithographic apparatus comprising an illumination optical system arranged to illuminate a pattern, and a projection optical system arranged to project an image of the pattern onto a substrate, wherein the lithographic apparatus comprises an illumination source as claimed in claim 35 or any of claims 44 to 55.

38. A lithographic system comprising:
a lithographic apparatus comprising an illumination optical system arranged to illuminate a pattern, and a projection optical system arranged to project an image of the pattern onto a substrate; and
an inspection apparatus as claimed in claim 36,
wherein the lithographic apparatus is arranged to use one or more parameters calculated by the inspection apparatus in applying the pattern to further substrates.

39. A gas delivery system for use in an illumination source, comprising at least a first gas delivery element operable to emit a first gas and a second gas delivery element operable to emit a second gas in such a way that a number density profile of the first gas is altered by the second gas.

40. A gas delivery system as claimed in claim 39, wherein the first gas is a high harmonic generation gas medium for the generation of high harmonic radiation and the second gas has a lower absorption of high harmonic radiation than the first gas.

41. A gas delivery system as claimed in claim 39 or 40, wherein the second gas is operable to modify a flow profile of the first gas such that number density of the gas falls sharply in the propagation direction of a pump radiation pulse after a pump radiation interaction region where the pump radiation pulse interacts with said first gas.

42. A gas delivery system as claimed in claim 39, 40 or 41, wherein the first gas delivery element is adjacent the second gas delivery element.

43. A gas delivery system as claimed in claim 39, 40 or 41, wherein the first gas delivery element and the second gas delivery element are arranged concentrically.

44. An illumination source for generating high harmonic radiation, the illumination system comprises the gas delivery system according to any one of the claims 39 to 43 and comprising a pump radiation source operable to emit pump radiation at the first gas.

45. An illumination source for generating high harmonic radiation, comprising:
a pump radiation source operable to emit pump radiation at a high harmonic generation gas medium thereby exciting said high harmonic generation gas medium within a pump radiation interaction region so as to generate said high harmonic radiation; and
an ionization radiation source operable to emit ionization radiation at the high harmonic generation gas medium to ionize said gas at an ionization region between the pump radiation interaction region and an optical output of the illumination source.

46. The illumination source of claim 45, wherein the ionization region is immediately adjacent said pump radiation interaction region.

47. The illumination source of claim 45 or 46, wherein the illumination source is arranged such that the ionization radiation ionizes said gas at the ionization region substantially simultaneously with the pump radiation exciting said high harmonic generation gas medium.

48. The illumination source of claim 45, 46 or 47, wherein the propagation direction of the ionization radiation is opposite to the propagation direction of the pump radiation.

49. The illumination source of claim 48, wherein the pump radiation source and the ionization radiation source are located on opposite sides of high harmonic generation gas medium.

50. The illumination source of claim 49, operable such that at least one of the wavelength, polarization or propagation angle of the pump radiation is different to that of the ionization radiation, thereby enabling the separation of returning pump radiation and/or ionizing radiation.

51. The illumination source of claim 45, 46 or 47, wherein the propagation direction of the ionization radiation is orthogonal to the propagation direction of the pump radiation.

52. The illumination source of claim 51, comprising an optical element operable to focus the ionization radiation on a line focus at the ionization region.

53. The illumination source of any of claims 45 to 52, comprising a common oscillator operable to provide both the pump radiation and ionization radiation.

54. The illumination source of any of claims 45 to 53, wherein said optical output comprises an aperture arranged to allow passage the pump radiation and to block the high harmonic radiation, the pump radiation having properties such that it is subject to greater deflection by refraction within the ionization radiation than the high harmonic radiation.

55. The illumination source of any of claims 45 to 54, comprising a dose control which controls timing of the ionization radiation with respect to the pump radiation, and/or the intensity of the ionization radiation, thereby controlling the absorption characteristics within the ionization region.

If in this document the term "metrology apparatus" is used, one may also read the term "inspection apparatus" at that position, and vice versa. In the context of this document said apparatuses can be used to determine characteristics of interest of a structure on a substrate. The characteristics of interest may be measurement values and may also be deviations from an expected pattern, such as the absence of structures, the presence of unexpected structures and changes in the expected pattern.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The invention claimed is:

1. A gas delivery system for use in an illumination source, comprising:
a gas delivery element arranged to direct gas in at least a first direction, wherein the gas delivery element comprises:
an optical input; and
an optical output,
wherein the input and the output define an optical path, the optical path being oriented in a second direction,
wherein the second direction is non-perpendicular and non-parallel to the first direction, and
wherein the optical input and optical output are arranged to allow pump radiation to pass through the gas to generate high harmonic radiation.

2. The gas delivery system of claim 1, wherein the first direction is at an obtuse angle relative to the second direction.

3. The gas delivery system of claim 1, wherein:
the optical input comprises an opening in a first wall of the gas delivery system, and
the optical output comprises an opening in an opposing wall of the gas delivery system.

4. The gas delivery system of claim 1, wherein:
the gas delivery element comprises a toroidal gas delivery component, the toroidal gas delivery component being arranged to deliver gas to the optical path in at least the first direction or arranged to deliver gas to the optical path in a plurality of first directions.

5. The gas delivery system of claim 1, further comprising:
a gas buffer element comprising a temperature controlling element.

6. The gas delivery system of claim 1, further comprising:
a filtering element operable to modify a flow profile of the gas and operable to provide a laminar flow profile of the gas.

7. The gas delivery system of claim 1, further comprising:
a gas jet shaping device operable to modify a flow profile of the gas, such that a number density of the gas falls sharply in the direction of the optical output after a pump radiation interaction region where pump radiation interacts with the gas.

8. The gas delivery system of claim 7, wherein:
the number density of the gas falls by at least a factor of 10 relative to that of the pump radiation interaction region within a drop off region immediately after the pump radiation interaction region in the direction toward the output, a length of the drop off region being 10% or smaller than a length of the pump radiation interaction region.

9. The gas delivery system of claim 7, wherein the modification of the flow profile is further operable to extend a length of the pump radiation interaction region relative to there being no gas jet shaping device present.

10. The gas delivery system of claim 9, wherein the length of the pump radiation interaction region is extended by more than 50% relative to there being no gas jet shaping device present.

11. The gas delivery system of claim 7, wherein:
the gas jet shaping device comprises an angled wall element located below the gas delivery element and obtusely angled relative to the first direction, and
the angled wall element is attached at a point adjacent a gas output of the gas delivery element, such that it extends below this gas output and at an angle towards the gas emitted.

12. The gas delivery system of claim 11, wherein:
the gas jet shaping element comprises an angled horizontal-cylindrical-segment open at its bottom end and the gas jet shaping element comprises a semi-cylindrical element.

13. An illumination source for generating high harmonic radiation, comprising:
a pump radiation source operable to emit pump radiation; and
the gas delivery system of claim 1, operable to receive the emitted pump radiation and to generate the high harmonic radiation.

14. An inspection apparatus for measuring a target structure on a substrate, comprising:
an illumination source of claim 13, for generating high harmonic radiation; and
a sensing element for receiving high harmonic radiation scattered by the target structure.

15. A lithographic system comprising:
a lithographic apparatus comprising an illumination optical system arranged to illuminate a pattern, and a projection optical system arranged to project an image of the pattern onto a substrate; and
the inspection apparatus of claim 14,
wherein the lithographic apparatus is arranged to use one or more parameters calculated by the inspection apparatus in applying the pattern to further substrates.

16. An lithographic apparatus comprising an illumination optical system arranged to illuminate a pattern, and a projection optical system arranged to project an image of the pattern onto a substrate,
wherein the lithographic apparatus comprises the illumination source of claim 13.

17. A gas delivery system for use in an illumination source, comprising:
a gas delivery element arranged to direct gas in at least a first direction, wherein the gas delivery element comprises:
an optical input and an optical output together defining an optical path, the optical path being oriented in a second direction; and
a gas jet shaping device operable to modify a flow profile of the gas such that a number density of the gas falls sharply in the direction of the optical output after a pump radiation interaction region where pump radiation interacts with the gas.

* * * * *

UNITED STATES PATENT AND TRADEMARK OFFICE
CERTIFICATE OF CORRECTION

| | |
|---|---|
| PATENT NO. | : 10,530,111 B2 |
| APPLICATION NO. | : 15/903392 |
| DATED | : January 7, 2020 |
| INVENTOR(S) | : Srivastava et al. |

Page 1 of 1

It is certified that error appears in the above-identified patent and that said Letters Patent is hereby corrected as shown below:

On the Title Page

Item (57), please replace "an optical input and an optical input" with – an optical input and an optical output –.

In the Claims

In Column 28, Line 39, Claim 16, please replace "An lithographic apparatus" with – A lithographic apparatus –.

Signed and Sealed this
Twelfth Day of May, 2020

Andrei Iancu
*Director of the United States Patent and Trademark Office*